United States Patent
Etzbach et al.

(10) Patent No.: US 6,335,462 B1
(45) Date of Patent: *Jan. 1, 2002

(54) POLYMERIZABLE OLIGOMESOGENES

(75) Inventors: Karl-Heinz Etzbach; Karl Siemensmeyer, both of Frankenthal; Peter Schuhmacher, Mannheim, all of (DE)

(73) Assignee: BASF Aktiengesellschaft, Ludwigshafen (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/308,634

(22) PCT Filed: Nov. 11, 1997

(86) PCT No.: PCT/EP97/06289

§ 371 Date: May 27, 1999

§ 102(e) Date: May 27, 1999

(87) PCT Pub. No.: WO98/23580

PCT Pub. Date: Jun. 4, 1998

(30) Foreign Application Priority Data

Nov. 27, 1996 (DE) .......................... 196 49 056

(51) Int. Cl.$^7$ .............................................. C07C 69/76
(52) U.S. Cl. ........................................................ 560/54
(58) Field of Search .......................................... 560/54

(56) References Cited

U.S. PATENT DOCUMENTS 4,997,591 A * 3/1991 Heppke et al. ........ 252/299.61

FOREIGN PATENT DOCUMENTS

| GB | 2 166 755 | | 5/1986 |
| WO | WO 95/16007 | * | 6/1995 |

OTHER PUBLICATIONS

N.H. Hartshorne, Liquid Crystals and Plastic Crystals, pp. 24–61, "Optical Properties of Liquid Crystals", 1974.

H. Baessler, Festkörperprobleme XI: Advances in Solid State Physics, pp. 99–133, "Liquid Crystals", 1971.

H. Baessler et al., The Journal of Chemical Physics, vol. 52, No. 2, pp. 631–637, "Helical Twisting Power of Steroidal Solutes in Cholesteric Mesophases", Jan. 15, 1970.

H. Baessler, et al., The Journal of Chemical Physics, vol. 51, No. 5, pp. 1846–1852, "Electric Field Effects on the Dielectric Properties and Molecular Arrangements of Cholesteric Liquid Crystals", Sep. 1, 1969.

H. Finkelmann, et al., Zeitschrift Für Naturforschung, vol. 28a, pp. 799–800. Helixinversion in Einem Binären Mischsystem Nematisch/Cholesterisch, 1973, (English Abstract only).

H. Stegemeyer, et al., Naturwissenschaflen, vol. 58, pp. 599–602, "Induzierung von Optischer Aktivität und Zirkulardichroismus in Nematischen Phasen Durch Chirale Moleküle", 1971, (English Abstract only).

H. Finkelmann, et al., Berichte Der Bunsen–Gesellschaft Für Physikalische Chemie, vol. 78, No. 9, pp. 869–874, "Beschreibung Cholesterischer Mischsysteme mit Einer Erweiterten Goossens–Theorie", 1974, English Abstract only).

I. Heynderickx, et al., Mol. Cryst. Liq. Cryst., vol. 203, pp. 113–126, "The Use of Cholesterically–Ordered Polymer Networks in Practical Applications", 1991.

F.H. Kreuzer, et al., Paper No. 7, 22$^{nd}$ Freiburg Congress on Liquid Crystals, one page, 1993, English Abstract Only.

D.J. Broer, et al., Die Makromolekulare Chemie, vol. 190, No. 10, pp. 3201–3215, "In–situ Photopolymerization of Oriented Liquid–Crystalline Acrylates, 4$^{a)}$ Influence of a Lateral Methyl Substituent on Monomer and Oriented Polymer Network Properties of a Mesogenic Diacrylate", 1989.

* cited by examiner

Primary Examiner—Barbara P. Badio
(74) Attorney, Agent, or Firm—Oblon, Spivak, McClelland, Maier & Neustadt, P.C.

(57) ABSTRACT

The compounds of the formula I

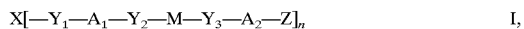

$$X[-Y_1-A_1-Y_2-M-Y_3-A_2-Z]_n \qquad I,$$

wherein the variables are as defined in the specification.

The compounds are suitable as alignment layers for liquid-crystalline materials, as photocrosslinkable adhesives, as monomers for the production of liquid-crystalline networks, as base material for the preparation of polymerizable liquid-crystal systems which can be doped by chiral compounds, as polymerizable matrix monomers for polymer-dispersed displays or as base material for polymerizable, liquid-crystalline materials for optical components, such as polarizers, retardation plates or lenses.

2 Claims, No Drawings

POLYMERIZABLE OLIGOMESOGENES

It is known that media which are anisotropic in shape can form liquid-crystalline phases, known as mesophases, on warming. The individual phases differ through the spatial arrangement of the major parts of the molecules on the one hand and through the molecular arrangement with respect to the long axes on the other hand (G. W. Gray, P. A. Winsor, Liquid Crystals and Plastic Crystals, Ellis Horwood Limited, Chichester, 1974). The nematic liquid-crystalline phase is distinguished by the fact that there is only one alignment long-distance ordering due to the long molecular axes lining up in parallel. Under the prerequisite that the molecules making up the nematic phase are chiral, a cholesteric phase forms, in which the long axes of the molecules form a helical superstructure perpendicular thereto (H. Baessler, Festkörperprobleme XI, 1971). The chiral moiety may be present either in the liquid-crystalline molecule itself or added to the nematic phase as a dope inducing the cholesteric phase. This phenomenon was first studied on cholesterol derivatives (eg. H. Baessler, M. M. Labes, J. Chem. Phys. 52 (1970) 631; H. Baessler, T. M. Laronge, M. M. Labes, J. Chem. Phys. 51 (1969) 3213; H. Finkelmann, H. Stegemeyer, Z. Naturforschg. 28a (1973) 799; H. Stegemeyer, K. J. Mainusch, Naturwiss. 58 (1971) 599; H. Finkelmann, H. Stegemeyer, Ber. Bunsenges. Phys. Chem. 78 (1974) 869).

The cholesteric phase has remarkable optical-properties: large optical rotation and pronounced circular dichroism caused by selective reflection of circular-polarized light within the cholesteric layer. The different colors to be observed depending on the viewing angle depend on the pitch of the helical superstructure, which is itself dependent on the twisting power of the chiral component. The pitch and thus the wavelength range of the selectively reflected light of a cholesteric layer can be varied, in particular, by changing the concentration of a chiral dope. Such cholesteric systems offer interesting opportunities for practical use. Thus, incorporation of chiral moieties into mesogenic acrylic esters and alignment in the cholesteric phase, for example after photocrosslinking, can give a stable, colored network, but the concentration of the chiral component therein cannot be changed (G. Galli, M. Laus, A. Angeloni, Makromol. Chem. 187 (1986) 289). Admixing of non-crosslinkable, chiral compounds with nematic acrylic esters can give by photocrosslinking a colored polymer which still contains high proportions of soluble components (I. Heyndricks, D. J. Broer, Mol. Cryst. Liq.

Cryst. 203 (1991) 113). Furthermore, random hydrosilylation of mixtures of cholesterol derivatives and acrylate-containing mesogens using defined cyclic siloxanes followed by photopolymerization allows the production of a cholesteric network in which the chiral component can comprise up to 50% of the material employed; however these polymers also contain significant amounts of soluble components (F. H. Kreuzer, R. Maurer, C. Müller-Rees, J. Stohrer, Paper No. 7, 22nd Freiburg Congress on Liquid Crystals, Freiburg 1993).

DE-A-35 35 547 describes a process in which a mixture of cholesterol-containing monoacrylates can be converted into cholesteric layers by photocrosslinking. However, the total proportion of the chiral component in the mixture is about 94%. Although a material of this type is not very mechanically stable as a pure side-chain polymer, an increase in the stability can, however, be achieved by means of highly crosslinking diluents.

In addition to the nematic and cholesteric networks described above, smectic networks are also known; these are prepared, in particular, by photopolymerization/photocrosslinking of smectic liquid-crystalline materials in the smectic liquid-crystalline phase. The materials used for this purpose are generally symmetrical liquid-crystalline bisacrylates, as described, for example, by D. J. Broer and R. A. M. Hikmet, Makromol. Chem., 190, (1989), 3201–3215. However, these materials have very high clearing points of >120° C., with the associated risk of thermal polymerization. If an $S_c$ phase exists, piezoelectric properties can be achieved by admixing chiral materials (R. A. M. Hikmet, Macromolecules 25, (1992), p. 5759).

The present invention relates to structures of the formula I $$X[-Y_1-A_1-Y_2-M-Y_3-A_2-Z]_n \qquad I,$$

where

X is a silicon-free, n-valent central unit, the radicals $A_1$ and $A_2$, independently of one another, are a direct bond or a spacer, the radicals $Y_1$, $Y_2$ and $Y_3$, independently of one another, are a direct bond, O, S, CO, OCO, COO, OCOO,

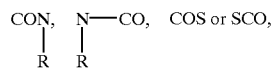

M is a mesogenic group,

Z is a polymerizable group, and n is a number from 2 to 6, where

R is hydrogen, or $C_1$- to $C_4$-alkyl, and the combination of M—$Y_3$ $A_2$—Z can be a cholesteryl radical.

The radicals X can be aliphatic, aromatic or cycloaliphatic and may additionally contain heteroatoms. Also suitable are divalent elements and groups such as O, S, $SO_2$ and CO.

X can be, in particular, $C_2$- to $C_{12}$-alkylene, -alkenylene or -alkynylene radicals, which may be interrupted by one or more O or S atoms or NR groups, or phenylene, benzylene or cyclohexylene or radicals of the formula

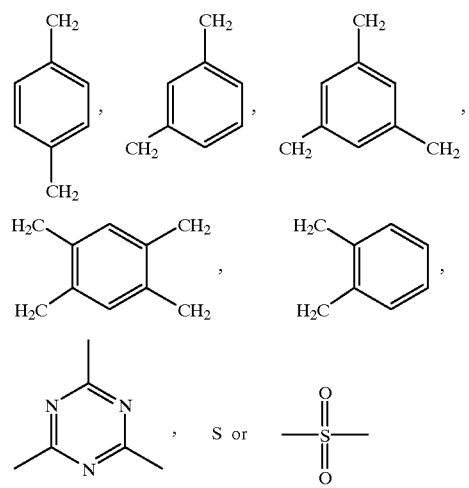

Examples of individual alkylene, alkenylene or alkynylene radicals are,

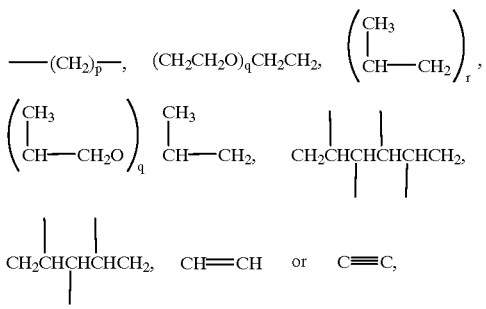

where
p is a number from 2 to 12,
q is a number from 1 to 3 and
r is a number from 1 to 6.

Suitable spacers are all groups which are known for this purpose; the spacers are usually linked to X via ester or ether groups or a direct bond. The spacers generally contain from 2 to 30, preferably from 2 to 12, in particular from 6 to 12, carbon atoms and may be interrupted in the chain, for example by O, S, NH or NCH$_3$. Suitable substituents for the spacer chain are fluorine, chlorine, bromine, cyano, methyl or ethyl.

Examples of representative spacers are the following:

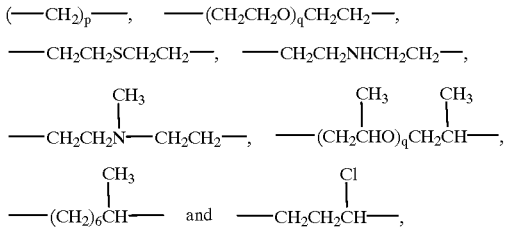

where
p and q are as defined above.

$Y_1$, $Y_2$ and $Y_3$ are preferably a direct bond, O, OCO, COO or OCOO.

The radicals M can in turn be the known mesogenic groups, in particular radicals containing aromatic or heteroaromatic groups. The mesogenic radicals conform, in particular, to the formula II $$(-T-Y^1)_s-T \qquad II,$$

where the radicals

T, independently of one another, are cycloalkylene, heterocycloalkylene, aromatic or heteroaromatic radicals, the radicals $Y^1$ independently of one another are O, COO, OCO, CH$_2$O, OCH$_2$, CH=N or N=CH or a direct bond, and s is from 1 to 3.

s is preferably 1 or 2.

$Y^1$ is preferably —COO—, —OCO— or a direct bond.

The radicals T are generally carbocyclic or heterocyclic aromatic ring systems, which may be substituted by fluorine, chlorine, bromine, cyano, hydroxyl or nitro, conforming, for example, to the following basic structures:

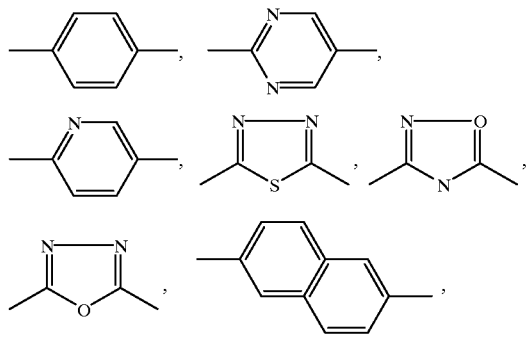

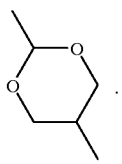

The mesogenic groups M are particularly preferably the following, for example:

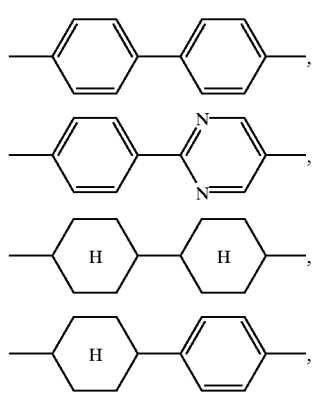

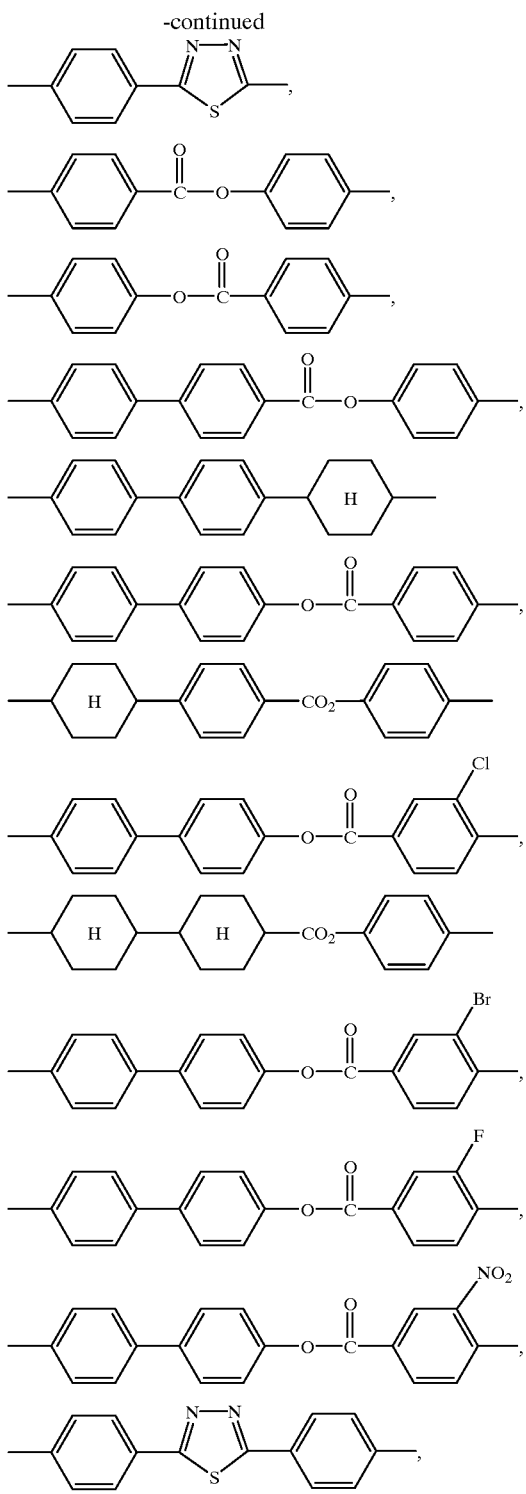

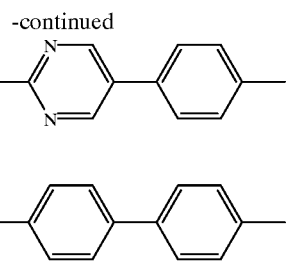

Preferred groups Z are those which can be polymerized by a photochemical initiation step, i.e. in particular groups of the structure: $CH_2=CH-$, $CH_2=CCl$, $CH_2=C(CH_3)-$ or 4-vinylphenylyl. Preference is given to $CH_2=CH-$, $CH_2=CCl-$ and $CH_2=C(CH_3)-$, particular preference being given to $CH_2=CH-$ and $CH_2=C(CH_3)-$.

General methods for the preparation of the compounds of the formula I are known from the literature, for example the reaction with dicyclohexylcarbodiimide (DCC) for the preparation of esters. Details on the reactions are given in the examples, where parts and percentages are by weight, unless stated otherwise.

The compounds of the formula I are liquid-crystalline and can form smectic, nematic or cholesteric phases, depending on the structure. They are suitable for all purposes for which liquid-crystalline compounds are usually used.

Novel compounds adopt an intermediate position between low-molecular-weight and polymeric liquid-crystalline compounds. In contrast to polymers, they can be prepared reproducibly, have substantially uniform structures and nevertheless have viscosities similar to those of polymers.

In order to establish desired properties, it may be expedient to use mixtures of compounds of the formula I or mixtures with other liquids, it being possible for these mixtures to be prepared in situ or by mechanical mixing.

The novel compounds are particularly suitable as alignment layers for liquid-crystalline materials, as photo-crosslinkable adhesives, as monomers for the production of liquid-crystalline networks, as base material for the preparation of polymerizable liquid-crystal systems which can be doped by chiral compounds, as polymerizable matrix monomers for polymer-dispersed displays or as base material for polymerizable liquid-crystalline materials for optical components, such as polarizers, retardation plates or lenses. They are furthermore suitable in combination with low-molecular-weight, polymerizable liquid-crystalline compounds as film formers.

The melting points in the examples were determined by means of a polarizing microscope. Temperature control was effected on a Mettler FP80/82 microscope heating stage.

EXAMPLES

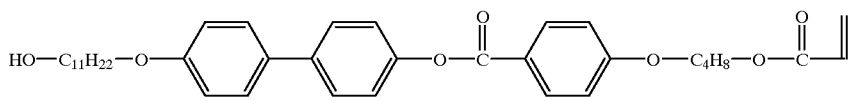

I

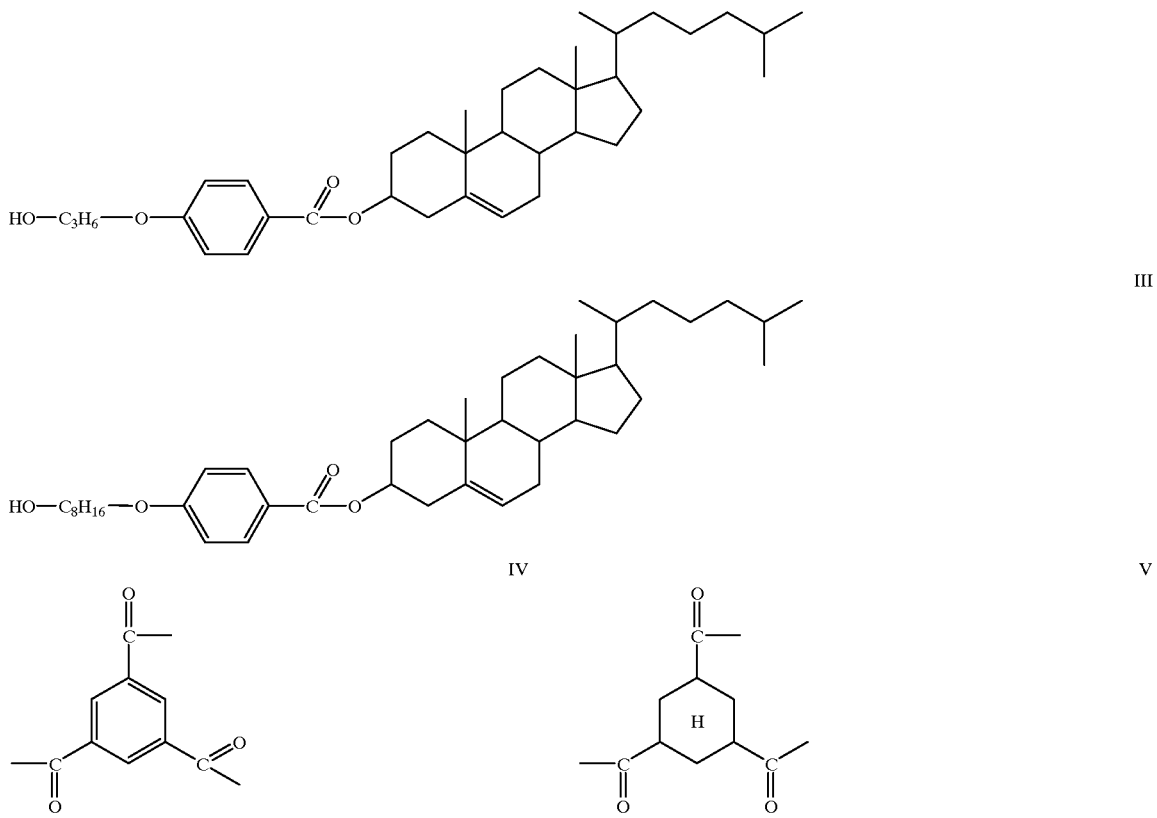

I, II and III are mesogens, and IV and V are central units.

Example 1

1 ml of a solution of 13.6 g (0.05 mol) of 1,3,5-cyclohexanetricarbonyl chloride in 50 ml of absolute toluene is added at 60° C. to a solution of 0.903 g (0.0015 mol) of I, 0.846 g (0.0015 mol) of II and 0.32 g of pyridine in 30 ml of toluene. The solution is stirred at 60° C. for one hour and then at room temperature overnight. 50 ml of water are added, and the mixture is neutralized by means of 15% strength hydrochloric acid. The organic phase is separated off, washed with water, dried using sodium sulfate and evaporated. Further purification is carried out by column chromatography (silica gel 60, toluene/ethyl acetate 3:1).

Yield: 1.45 g Phase behavior: n* polymerized the compounds in the table below were prepared by methods similar to that in Example 1:

| Ex. | Mesogen 1 | Mesogen 2 | Mixing ratio | Central unit | Phase behavior |
|---|---|---|---|---|---|
| 2 | I | II | 1:1 | IV | x 66 n* polymerized |
| 3 | I | III | 1:1 | V | n* polymerized |
| 4 | I | III | 1:1 | IV | n* polymerized |
| 5 | I | II | 3:2 | V | g s 96 n* 130 polymerized |
| 6 | I | II | 3:2 | IV | x 96 n* polymerized |
| 7 | I | III | 3:2 | V | x 68 n* polymerized |
| 8 | I | III | 3:2 | IV | x 38–42 n* polymerized | x = unidentified phase
g = glass state
s = smectic phase
n or n* = nematic or chiral nematic phase
i = isotropic phase
c = crystalline The above compounds are all converted into polymers at elevated temperature.

Example 9

0.66 g (0.03 mol) of benzene-1,2,4,5-tetracarboxylic anhydride and 3.8 g of II are suspended in 15 ml of DMF, and the mixture is stirred at 110° C. for 8 hours. The reaction product is precipitated by pouring into water, filtered off with suction, washed with water, dried at 50° C. under reduced pressure and recrystallized from ethanol/toluene.

Yield: 2,7 g Solidification: 170–215° C.

1.49 g (0.001 mol) of the resultant reaction product, 1.2 g (0,002 mol) of I and 0.03 g (0.00022 mol) of pyrrolidinopyridine are dissolved in 40 ml of methylene chloride. 0.45 g (0.0022 mol) of dicyclohexylcarbodiimide are then added, and the mixture is stirred at room temperature overnight.

The solution is filtered and evaporated, and the precipitated residue is chromatographed on silica gel 60 using toluene/glacial acetic acid 3:1.

Yield: 1 g Phase behavior: x 46–70 n*160–180 i.

Example 10

The isomeric compounds are prepared by methods similar to that in Example 9, where benzene-1,2,4,5-tetracarboxylic anhydride is esterified first with III and then with I.

Yield: 500 mg Phase behavior: c 61–70 n*168–186 i.

Example 11

Preparation of

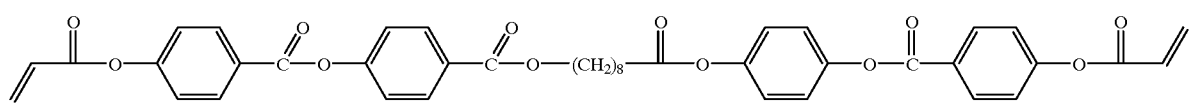

114 g (0.5 mol) of 4-benzyloxybenzoyl chloride are dissolved in a mixture of 150 ml of absolute $CH_2Cl_2$ and 9.6 g of-pyridine. 7.3 g (0.55 mol) of 1,8-octandiol are then introduced at from 10 to 15° C., and the mixture is stirred overnight. The reaction product is precipitated by pouring into water and recrystallized from 250 ml of ethanol.

Yield: 25.1 g (=88.7% of theory; Melting point: 90–91° C.

24.9 g (0.044 mol) of reaction product are dissolved in a mixture of 150 ml of toluene and 100 ml of ethanol, and 5.1 g of Raney nickel are added. The mixture is then hydrogenated for 1.5 hours at from 45 to 50° C. with vigorous stirring. The $H_2$ consumption is 2.1 l under atmospheric pressure. The reaction product is separated off from the catalyst and filtered off. Further purification was unnecessary.

Yield: 16.8 g (=98.9% of theory); Melting point: 182–183° C.

0.97 g (0.0025 mol) of the resultant compound, 0.1 g of pyrrolidinopyridine and 1.53 g of compound of the formula

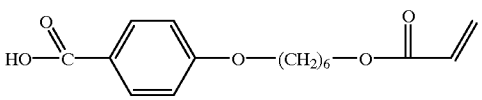

are dissolved in 50 ml of tetrahydrofuran. A solution of 1.5 g of dicyclohexylcarbodiimide in 5 ml of tetrahydrofuran is then added at from 5 to 10° C., and the mixture is stirred at 50° C. for 4 hours and subsequently at room temperature overnight. The precipitated solid is filtered off, and the solution is evaporated. The residue is purified by column chromatography (silica gel 60, toluene/glacial acetic acid 3:1).

Yield: 0.45 g Phase behavior: c 77–82 n polymerized.

The following compounds can be prepared analogously:

Example 12

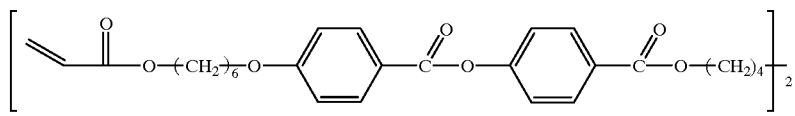

Phase behavior: c 116–144 n 154–156 i

Example 13

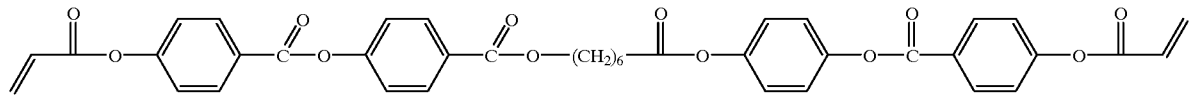

Phase behavior: c 148 n 185 i

The following compounds can also be prepared analogously to Example 1:

Example 14

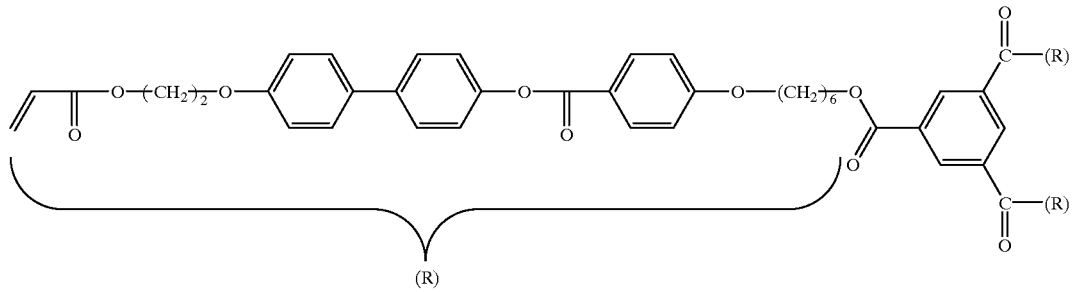

Phase behavior: c 86 n→polymerized

Example 15

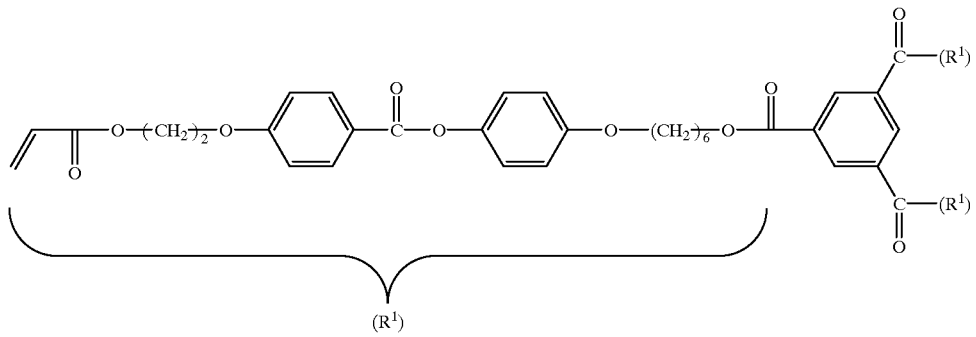

Phase behavior: c 100 n→polymerized

Example 16

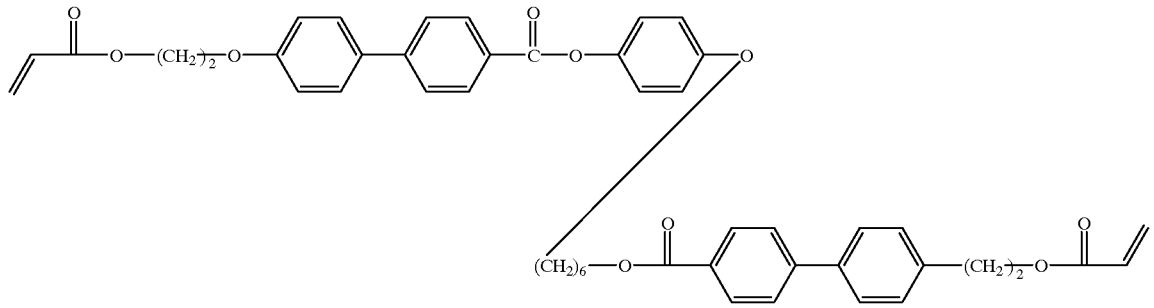

4.2 g (0.02 mol) of the compound of the formula

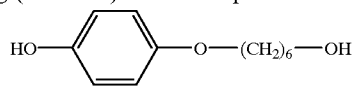

are dissolved in 50 ml of tetrahydrofuran and 1.58 ml of pyrridine. 6.77 g (0.04 mol) of the compound of the formula

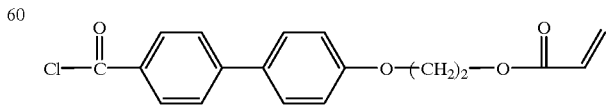

are added to this solution, and the mixture is stirred overnight. The reaction mixture is poured into HCl-acidified water, the solid is filtered off and taken up in methyl tert-butyl ether, and the resultant organic phase is washed by shaking repeatedly with water. The solid obtained after evaporation is recrystallized from ethanol/toluene.

Yield: 3.45 g; Phase behavior: c 133 n→polymerized.

Example 17

60.4 g (0.4 mol) of methyl hydroxybenzoate and 2.6 g (0.02 mol) of zinc(II) chloride are suspended in 180 ml of methylene chloride. After the mixture has been stirred at room temperature for 20 minutes, 16.2 (0.2 mol) of disulfur dichloride, dissolved in 20 ml of methylene chloride are added at room temperature over the course of 2 hours, and the mixture is then refluxed for 1½ hours and stirred at room temperature for 48 hours. The reaction product is filtered off with suction, washed with methylene chloride, taken up in water and boiled for 1 hour. After cooling, the product is filtered off and dried.

Yield: 11.8 g Melting point: 170–172° C.

5.01 g (0.015 mol) of the resultant compound are dissolved in 50 ml of methylene chloride and 2.61 g (0.033 mol) of pyridine. 10.65 g (0.033 mol) of the compound of the formula

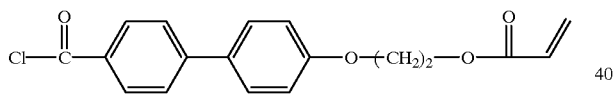

dissolved in 20 ml of methylene chloride are added to this solution, and the mixture is then stirred at room temperature overnight. For work-up, the reaction mixture is poured into water, and the precipitated solid is filtered off with suction and purified by chromatography (silica gel 60, toluene/THF 3:1)

Yield: 9.45 g c 159→polymerized.

The compound conforms to the formula

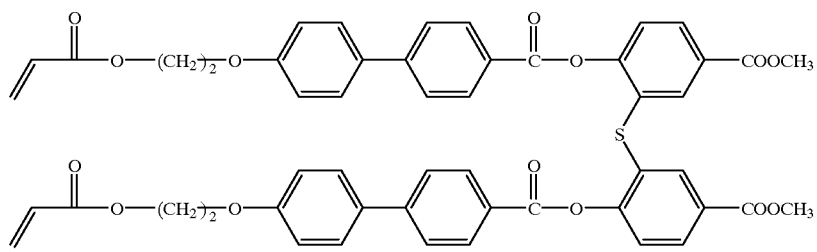

Example 18

The compound of the formula

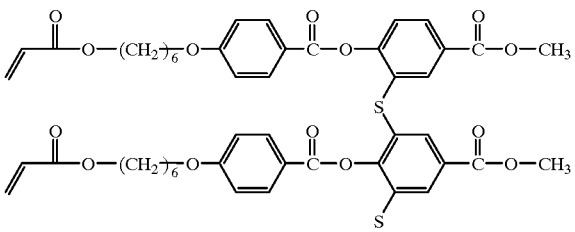

is also prepared analogously to Example 17. It polymerizes on heating.

Example 19

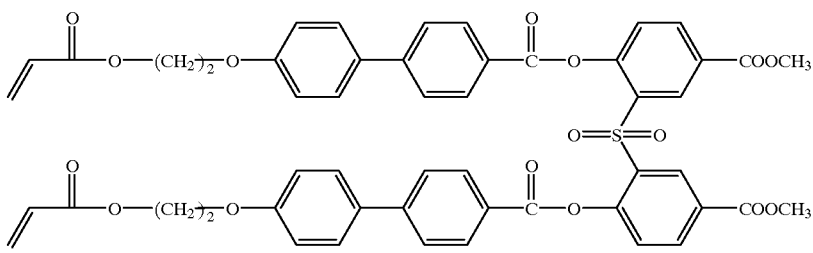

4.34 g (0.015 mol) of the compound of the formula

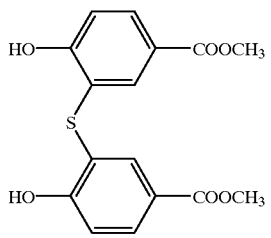

are dissolved in 40 ml of glacial acetic acid, and 3.24 g (0.0286 mol) of perhydrol (30% strength in water) are added at room temperature.

The mixture is then stirred at 100° C. for 1 hour. After cooling, the product is precipitated by pouring into water, filtered off with suction, washed repeatedly with water and dried at 50° C. under reduced pressure.

Yield: 4.5 g Melting point 210–221° C.

Further reaction of the resultant compound analogously to Example 17 gives the above compound.

Yield: 2.75 g c 199 polymerizes on transition into the liquid-crystalline phase.

We claim:

1. A compound of the formula I $$X(-Y_1-A_1-Y_2-M-Y_3-A_2-Z)_n \quad \quad I,$$

where

X is a non-chiral alkylene radical $A_1$ and $A_2$, independently of one another, are a direct bond or an alkylene spacer, $Y_1$ is COO or OCO, $Y_2$ is a direct bond, $Y_3$ is O or S, M is a radical of the formula $(-T-Y^1)_s-T$ where the radicals T, independently of one another, are aromatic or heteroaromatic radicals, $Y^1$ is COO or OCO s is from 1 to 3, Z is a radical of the formula $$CH_2=CH, CH_2=CCl \text{ or } CH_2=C(CH_3)$$

n is a number from 2 to 6, and wherein the compound of formula I is non-chiral.

2. A liquid crystal display comprising a compound of claim 1 incorporated into alignment layers for liquid-crystalline materials, or used as photocrosslinkable adhesives, or as monomers for the production of liquid-crystalline networks, or as a base material for the preparation of a polymerizable liquid-crystal system which can be doped with chiral compounds, or as polymerizable matrix monomers for polymer-dispersed displays or as a base material for polymerizable liquid-crystalline materials for optical components, polarizers, retardation plates or lenses, or in combination with low-molecular-weight, polymerizable liquid-crystalline compounds as film formers.

* * * * *